United States Patent [19]

Villa et al.

[11] Patent Number: 4,873,233
[45] Date of Patent: Oct. 10, 1989

[54] 17-SUBSTITUTED ANDROSTA-1,4-DIEN-3-ONE DERIVATIVES

[75] Inventors: Vittoria Villa; Enrico di Salle; Paolo Lombardi, all of Milan, Italy

[73] Assignee: Farmitalia Carlo Erba S.p.a., Milan, Italy

[21] Appl. No.: 242,855

[22] Filed: Sep. 12, 1988

[30] Foreign Application Priority Data

Sep. 11, 1987 [GB] United Kingdom ............. 8721384

[51] Int. Cl.⁴ .................. A61K 31/56; C07J 1/00
[52] U.S. Cl. .................. 514/179; 260/397.4
[58] Field of Search ............. 514/179; 260/397.4

[56] References Cited

PUBLICATIONS

Chemical Abstracts; vol. 75 (1971) #150180w; Raab.

Primary Examiner—Douglas W. Robinson
Assistant Examiner—Joseph A. Lipovsky
Attorney, Agent, or Firm—Armstrong, Nikaido, Marmelstein, Kubovcik & Murray

[57] ABSTRACT

The invention relates to new 17-hydroxy androsta-1,4-diene-3-one derivatives of the following formula

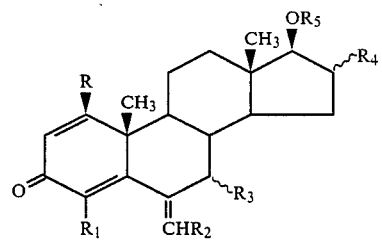

wherein
each of R and $R_3$, independently, is hydrogen or $C_1$–$C_6$ alkyl;
$R_1$ is hydrogen, halogen or $C_1$–$C_6$ alkyl;
$R_2$ is hydrogen or $C_1$–$C_6$ alkyl;
$R_4$ is hydrogen or fluorine;
$R_5$ is (a) hydrogen or $C_1$–$C_6$ alkyl; (b) phenyl unsubstituted or substituted by one or two substituents independently chosen from $C_1$–$C_6$ alkyl, halogen and amino; (c) an acyl group; or (d) a hydroxy protecting group; and the pharmaceutically acceptable salts thereof, which are useful in therapy, in particular as anti-cancer agents.

8 Claims, No Drawings

17-SUBSTITUTED ANDROSTA-1,4-DIEN-3-ONE DERIVATIVES

The present invention relates to novel 17-substituted androsta-1,4-dien-3-one derivatives, to a process for their preparation, to pharmaceutical compositions containing them, and to their use in therapy.

Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas. Estrogens are also involved in the pathogenesis of benign prostatic hyperplasia.

Endogenous estrogens are ultimately formed from either androstenedione or testosterone as immediate precursors. The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours.

Known steroidal substances which have been reported to be endowed with an aromatase-inhibiting action are, for example, $\Delta^1$-testololactone [U.S. Pat. No. 2,744,120], 4-hydroxy-androst-4-ene-3,17-dione and esters thereof [see, for example, U.S. Pat. No. 4,235,893], 10-(1,2-propadienyl)-estr-4-ene-3,17-dione [U.S. Pat. No. 4,389,762], 10-(2-propynyl)-estr-4-ene-3,17-dione [J. Am. Chem. Soc., 103, 3221 (1981) and U.S. Pat. No. 4,322,416], 19-thioandrostene derivatives (Europ. Pat. Appl. No. 100566), androsta-4,6-diene-3,17-dione, androsta-1,4-6-triene-3,17-dione [G.B. Pat. Appl. No. 2,100,601A] and androsta-1,4-diene-3,17-dione [Cancer Res. (Suppl.) 42, 3327 (1982)].

The novel compounds of the present invention are potent inhibitors of estrogen biosynthesis, by virtue of their ability to inhibit the aromatization of androgens into estrogens.

Furtherly, the novel compound have an androgenic activity which could contribute, through a decrease in gonadotropin secretion, to their inhibitory effect on estrogen synthesis. In fact, e.g., in the premenopausal situation aromatose synthesis is regulated by gonadotropins and the novel compounds can be effective in decreasing estrogens at two levels, by inhibiting aromatase activity (aromatase inhibitory effect) and aromatase synthesis (antigonadotropic effect).

The present invention provides compounds having the following general formula (I)

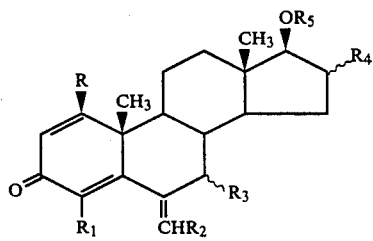

wherein each of R and $R_3$, independently, is hydrogen or $C_1$-$C_6$ alkyl;
$R_1$ is hydrogen, halogen or $C_1$-$C_6$ alkyl;
$R_2$ is hydrogen or $C_1$-$C_6$ alkyl;
$R_4$ is hydrogen or fluorine;
$R_5$ is (a) hydrogen or $C_1$-$C_6$ alkyl; (b) phenyl unsubstituted or substituted by one or two substituents independently chosen from $C_1$-$C_6$ alkyl, halogen and amino; (c) an acyl group; or (d) a hydroxy protecting group; and the pharmaceutically acceptable salts thereof.

A $C_1$-$C_6$ alkyl group is preferably a $C_1$-$C_4$ alkyl group, in particular methyl, ethyl, propyl or t-butyl, more preferably methyl or ethyl. From these examples it appears clear that an alkyl radical may be a branched or straight chain group. A halogen atom is e.g. chlorine, fluorine, or bromine, in particular chlorine or fluorine, more preferably fluorine. When $R_5$ is an acyl group the acid residue may be a residue of a physiologically tolerable acid. Preferred examples of physiologically tolerable acids are carboxylic acids containing up to 15 carbon atoms. The carboxylic acids may also be unsaturated, branched, polybasic or substituted in the usual manner, for example, by oxo, hydroxyl or amino groups or by halogen atoms.

Also suitable are cycloaliphatic, aromatic, mixed aromatic-aliphatic or heterocyclic acids, which can also be substituted in a suitable manner. Examples of such acids are acetic acid, propionic acid, butyric acid, valeric acid, caproic acid, oenanthic acid, undecylic acid, trimethylacetic acid, diethylacetic acid tert.-butylacetic acid, phenyl-acetic acid, cyclopentylpropionic acid, oleic acid, lactic acid, monochloroacetic acid, dichloroacetic acid, trichloroacetic acid, aminoacetic acid, succinic acid, adipic acid, benzoic acid and nicotinic acid. Also suitable are the common inorganic acids, for example sulphuric acid, nitric acid and phosphoric acid.

More preferably when $R_5$ is an acyl group, the acid residue is a residue of an acid, in particular, selected from the group including acetic, propionic, valeric, undecylic, trimethylacetic, phenylacetic, cyclopentylpropionic, oleic, monochloro acetic, amino acetic, succinic, benzoic, sulphuric and phosphoric acid.

An-$OR_5$ hydroxy protected group is a group, especially an ether group, convertible to hydroxy group under mild reaction conditions, e.g. acid hydrolysis. Examples are acetalic ethers, enolethers and silylethers. Particularly preferred hydroxy protecting groups are:

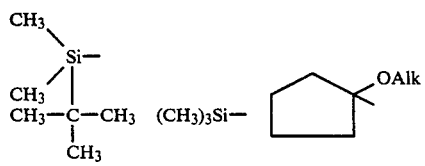

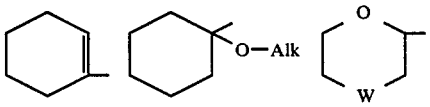

wherein W is —O— or —CH$_2$—, and Alk is a lower alkyl group; more preferably, they are 2'-tetrahydropyranyl or trimethylsilyl. Lower alkyl is typically $C_1$-$C_6$ alkyl, preferably $C_1$-$C_4$ alkyl.

As already said, the invention includes also the pharmaceutically acceptable salts of the compounds of formula (I). Preferred salts according to the invention are the salts of the compounds of formula (I), wherein $R_5$ is the the acyl residue of a polybasic, preferably dibasic, acid with pharmaceutically acceptable bases.

The bases may be both inorganic bases such as, for instance, alkali metal, e.g. sodium or potassium, or alkaline earth metal, e.g. calcium or magnesium, hydroxides, and organic bases such as, for instance, alkyl amines, e.g. methylamine or triethylamine, aralkylamines, e.g. benzylamine, dibenzylamine, α- or β-phenylethylamine, or heterocyclic amines such as, e.g., piperidine, 1-methyl-piperidine, piperazine or morpholine.

The formula reported above for the compounds of the invention includes all the possible isomers, in particular Z and E isomers, both separately and as mixture, of the compounds of formula (I) in which $R_2$ is $C_1$-$C_6$ alkyl.

In the formulae of this specification the broken lines (∣∣∣∣) indicate that the substituents are in the α-configuration, i.e. below the plane of the ring, while the heavy solid lines (▶) indicate that the substituents are in the β-configuration, i.e. above the plane of the ring; the wavy lines (∼) indicate that the groups may be both in the α-configuration or in the β-configuration.

Preferred compounds of the invention are the compounds of formula (I), wherein

R and $R_3$ are independently hydrogen or $C_1$-$C_4$ alkyl;
$R_1$ is hydrogen, fluorine, chlorine or $C_1$-$C_4$ alkyl;
$R_2$ is hydrogen or $C_1$-$C_4$ alkyl.
$R_4$ is hydrogen or fluorine;
$R_5$ is hydrogen, $C_1$-$C_4$ alkyl or an acyl group deriving from an acid selected from the group comprising acetic, propionic, valeric, undecylic, phenylacetic, cyclopentylpropionic, oleic, aminoacetic, succinic, sulphuric and phosphoric acid; and the pharmaceutically acceptable salts thereof.

Examples of specific compounds of the invention are:
6-methylenandrosta-1,4-diene-17β-ol-3-one;
1-methyl-6-methylenandrosta-1,4-diene-17β-ol-3-one;
7-methyl-6-methylenandrosta-1,4-diene-17β-ol-3-one;
4-chloro-6-methylenandrosta-1,4-diene-17β-ol-3-one;
4-chloro-1-methyl-6-methylenandrosta-1,4-diene-17β-ol 3-one:
4-chloro-7-methyl-6-methylenandrosta-1,4-diene-17β-ol-3-one;
6-methylenandrosta-1,4-diene-17β-ol-3-one-17-propionate;
1-methyl-6-methylenandrosta-1,4-diene-17β-ol-3-one-17-propianate;
7-methyl-6-methyleneandrosta-1,4-diene,17β-ol-3-one-17-propionate;
6-methylenandrosta-1,4-diene-17β-ol-3-one-17-sulphate;
1-methyl-6-methylenandrosta-1,4-diene-17β-ol-3-one-17-sulphate; and
7-methyl-6-methylenandrosta-1,4-diene-17β-ol-3-one-17-sulphate; and
where appropriate the pharmaceutically acceptable salts thereof.

The compounds of the invention and the salts thereof can be obtained by a process comprising:
(a) dehydrogenating a compound of formula (II)

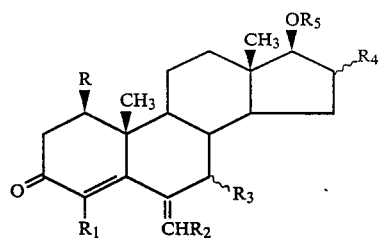

wherein
R, $R_1$, $R_2$, $R_3$, $R_4$ and $R_5$ are as defined above; or
(b) reacting a compound of formula (III)

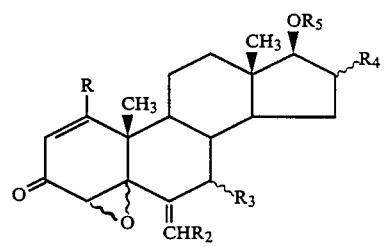

wherein
R, $R_2$, $R_3$, $R_4$ and $R_5$ are as defined above, with a hydrohalogenating agent, thus obtaining a compound of formula (I) wherein $R_1$ is halogen and R, $R_1$, $R_2$, $R_3$, $R_4$ and $R_5$ are as defined above; or
(c) reacting of a compound of formula (IV)

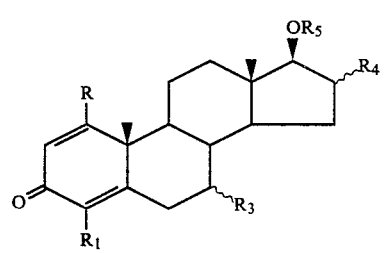

wherein R, $R_1$, $R_3$, $R_4$ and $R_5$ are as defined above, with a formaldehyde source, preferably paraformaldehyde or an aldehyde of formula (V) $R'_2CHO$, wherein $R'_2$ is $C_1$-$C_6$ alkyl, and an amine of formula (VI), or a salt thereof,

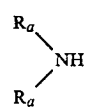

wherein
each $R_a$ group, which may be the same or different, is lower alkyl, and if desired, converting a compound of formula (I) into another compound of formula (I), and/or salifying a compound of formula (I) or obtaining a free compound of formula (I) from a salt thereof and/or separating a mixture of isomers of compound of formula (I) into the single isomers. The dehydrogenation of a compound of formula (II) may be carried out by treatment with a suitable dehydrogenating agent, e.g. dichlorodicyanobenzoquinone (DDQ), selenium dioxide or chloranil. Preferably such reaction is performed by treatment with DDQ, in an inert solvent, such as dioxane, benzene, toluene or dichloromethane, at a temperature ranging from about 40° C. to about 120° C. and reaction times ranging from about 12 hours to about 72 hours.

The hydro-halogenating agent which reacts with a compound for formula (III) is e.g. a hydrohalic acid or a trihaloborane. The reaction of a compound of formula (III) with a hydrohalic acid or a trihaloborane may be carried out according to known methods, e.g. Camerino et al., 1956, Il Farmaco 11, 586 and A. Bowers et al., 1958, Tetrahedron 3, 14, respectively. When the hydrohalic acid is the hydrochloric or hydrobromic one, such reaction is preferably performed in acetic acid or ethanol, at a temperature ranging from about 0° C. to about 100° C.

When a trihaloborane is used, e.g. boron trifluoride, the reaction is preferably performed in an inert solvent, such as diethyl ether, benzene or dichloromethane, at a temperature ranging from about −30° C. to about 50° C.

In a compound of formula (VI), $R_a$ lower alkyl is e.g. $C_1$-$C_4$ alkyl, preferably it is methyl or ethyl, in particular methyl. A salt of a compound of formula (VI) is e.g., a salt with an inorganic acid, preferably a hydrohalic acid, in particular the hydrochloride.

The reaction of a compound of formula (IV) with a formaldehyde source or an aldehyde of formula (V) and a salt of a compound of formula (VI) is preferably carried out in a high boiling alcohol, in particular isopentanol, at temperatures of about 130° C. or higher than 130° C., and for reaction times ranging from about 3 hours to about one day. In a preferred embodiment the formaldehyde source or aldehyde of formula (V) is first reacted with a salt of a compound of formula (VI) and then, to the Mannich salt so obtained, a compound of formula (IV) is added.

As stated above a compound of formula (I) may be converted into another compound of formula (I) by known methods. For example, a free hydroxy group may be etherified by reaction with a suitable alkyl or phenyl halide in the presence of a base such as NaOH, KOH, $Na_2CO_3$, $K_2CO_3$, NaH, $NaNH_2$, sodium methoxide or sodium ethoxide in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C.

Analogously a free hydroxy group may be converted into a protected hydroxy group by the usual procedures known in the art, e.g. a silyl ether may be obtained by reaction with the appropriate allyl halide in the presence of a base, using conventional procedures. Furthermore an etherified hydroxy group may be converted into a free hydroxy group with known methods, for example, by treatment with pyridine hydrochloride or with a strong acid such as HBr or HI, or with a Lewis acid such as $BF_3$ or $AlCl_3$ or $AlBr_3$ in presence of a thiol, or with trimethyliodosilane. A free hydroxy group may be esterified, thus obtaining a compound of formula (I), wherein $R_5$ is an acyl group as defined above according to known methods. For example a free hydroxy group may be converted into an esterified hydroxy group by treatment with a suitable acylating agent, e.g., a reactive derivative of a suitable acid, such as an anhydride or a halide, preferably the chloride thereof, and in the presence of a basic agent, preferably an organic base, such as pyridine. The reaction may be carried out at a temperature ranging from about room temperature to about 100° C.

When required, reactive functional groups may be protected with suitable protecting reagents, which may be removed after the reaction by known methods, which are available from the chemical literature.

Also the optional salification of a compound of formula (I) as well as the conversion of a salt into the free compound and the separation of a mixture of isomers of a compound of formula (I) into the single isomers may be carried out according to conventional methods known per se.

For example the separation of a mixture of geometric isomers may be performed by fractional crystallization or by separation through column chromatography.

A compound of formula (II) may be obtained starting from a compound of formula (VII) known per se, according to known methods, e.g. according to the method of K. Annen, 1982, Synthesis, 34. Preferably a compound of formula (VII) is reacted with unsubstituted or appropriately $C_1$-$C_6$ alkyl substituted formaldehyde-diethylacetal in refluxing chloroform, in the presence of phosphoryl chloride and sodium acetate. Alternatively the same reaction may be carried out in other inert solvents, e.g. 1,2-dichloroethane, diethylether or dioxane, and in the presence of other suitable condensing agents, e.g. phosphorus pentoxide or p-toluenesulfonic acid.

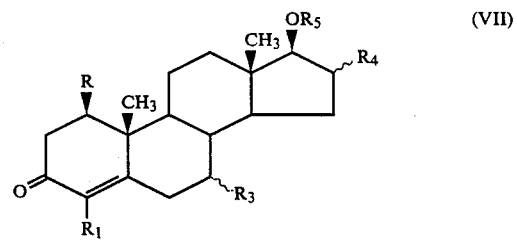

(VII)

Compounds of formula (III) may be obtained according to known procedures, for example as shown in the following reaction scheme:

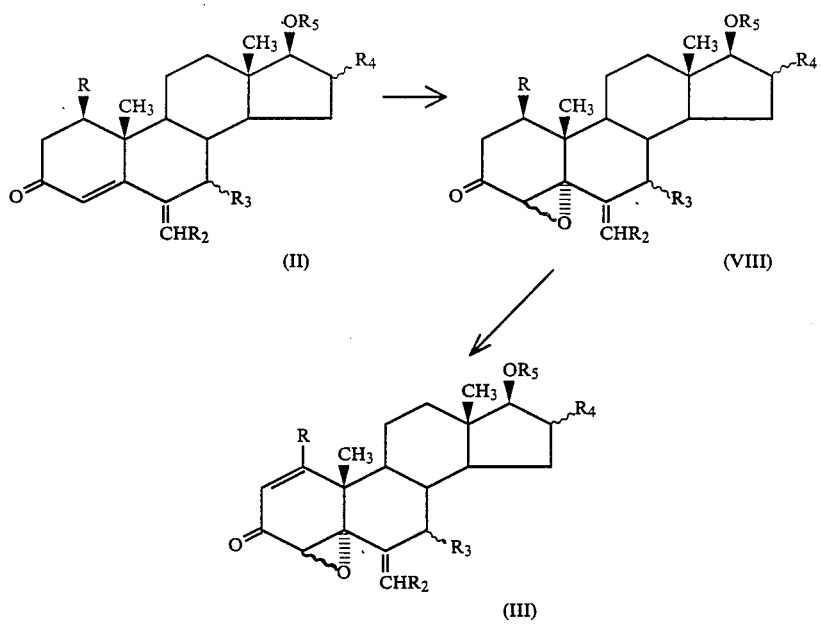

(II) → (VIII)

(III)

Epoxidation of a compound of formula (II) to obtain a compound of formula (VIII) may be carried out by treatment with a suitable oxidizing agent, preferably concentrated, e.g. 36% $H_2O_2$, in alcoholic alkali hydroxide solution, preferably KOH or NaOH in methanol, at a temperature e.g. ranging from 0° to 25° C. for from about 2 hours to several days. Dehydrogenation of a compound of formula (VIII) to obtain a compound of formula (III) may be carried out by treatment with a suitable dehydrogenating agent, e.g. with dichlorodicyanobenzoquinone in a refluxing solvent according to H. J. Ringold et al. 1962, Chemistry and Industry 211. Compounds of formula (IV) may be obtained starting from compounds of formula (VII). The introduction of a double bond at position 1 can be accomplished according to the previously described methods (H. J. Ringold et al. 1962, Chem. and Ind. 211).

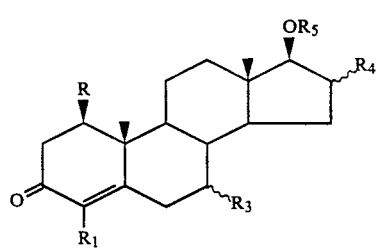

(VII)

The compounds of the present invention are inhibitors of the biotransformation of androgens into estrogens, i.e., they are steroidal aromatase inhibitors.

The inhibition of aromatase activity by these compounds was demonstrated e.g. by employing the in vivo test in rats described by Brodie (A. M. H. Brodie et al. Steroids, 38, 693, 1981), slightly modified.

Adult female rats were twice treated subcutaneously with 100 I.U. pregnant mares' serum gonadotropin (PMSG) at 4 days' interval, in order to increase ovarian aromatase activity. Three days after the second PMSG treatment, groups of 6 animals each were given orally and/or subcutaneously the novel aromatase inhibitors. Animals were killed 24 h later, microsomes were isolated from ovaries and their aromatase activity determined with the assay of Thompson and Siiteri (J. Biol. Chem. 249, 5364, 1974). This method determines the rate of aromatization by measuring the release of $^3H_2O$ from [$1\beta,2\beta$-$^3H$]-androstenedione. The incubations were carried out for 30 min. in 1 ml incubation volume containing 0.1 mg of microsomal proteins, 100 nM [$^3H$]-androstenedione and 100 uM NADPH.

The new compounds showed a relevant inhibition of aromatase activity.

The androgenic property of the compounds of the present invention was demonstrated e.g. by their binding affinity to androgen receptor.

Binding affinity to cytoplasmic androgen (rat prostate) receptors was determined by standard dextran-coated charcoal adsorption technique (Raynaud J. P. et al. J. Steroid. Biochem. 6, 615–622, 1975).

Prostatic tissue, obtained from both adrenalectomized and orchidectomized Sprague-Dawley rats, was homogenized (1:10 weight:vol ratio) in 10 mM Tris-HCl PH 7.4, containing 1.5 nM EDTA and 1 mM dithiothreitol, in motor driven tissue grinders. The homogenate was centrifuged at 105,000×g for 1 h at 2° C. Aliquots of cytosol (0.2 ml) were incubated for 2 h at 0° C. with various concentrations of the test compounds, in duplicate, and a fixed amount of [$^3H$]-5α-dihydrotestosterone (DHT, final concentration 1 nM in 0.4 ml of incubation volume). Then, free radioactivity was adsorbed on 0.2 ml of dextran-coated charcoal suspension and after centrifugation at 1,500×g for 10 min, the bound radioactivity in the supernatant was determined by liquid scintillation in RIaluma.

The concentration of each compound required to reduce specific $^3H$-DHT binding by 50% ($IC_{50}$) was determined from a plot of bound radioactivity vs. log competitor concentration.

The results obtained with 6-methylenandrosta-1,4-diene-17$\beta$-ol-3-one, i.e. a representative compound according to the present invention and the structurally related prior-art compound 6-methylenandrosta-1,4-diene-3,17-dione, described in Published British patent application No. 2177700, are reported in the following table:

TABLE

| Androgen receptor binding affinity | |
|---|---|
| Compound | IC$_{50}$ (nM)* |
| 6-methylenandrosta--1,4-diene-17β-ol-3-one | 610 ± 82 |
| 6-methylenandrosta--1,4-diene-3,17-dione | 8 ± 2 |

*Mean ± S.E. of 3 experiments

From the table it appears that the compound of the present invention 6-methylenandrosta-1,4-diene-17β-ol-3-one shows a very high affinity to the androgen receptor, being 76 times more potent than the correspondent 17-cheto-derivative previously described.

By virtue of their ability to inhibit aromatase and, consequently, to reduce estrogen levels, the new compounds are useful in the treatment and prevention of various hormone dependent diseases, i.e., breast, endometrial, ovarian and pancreatic cancers, gynecomastia, benign breast disease, endometriosis, polycystic ovarian disease and precocious puberty.

The new compounds can find also use for the treatment of male infertility associated with oligospermia and for female fertility control, by virtue of their ability to inhibit ovulation and egg nidation.

In view of their high therapeutic index, the compounds of the invention can be used safely in medicine. For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 200–400 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

0.50 of 6-methylenandrost-4-ene-17β-ol-3-one and 0.57 g of dichlorodicyanobenzoquinone are refluxed in 20 ml of anhydrous dioxane for about 15 hours. To remove the DDQ the suspension is filtered through alumina. After evaporation of the solvent the residue is dissolved in ethyl acetate, the organic layer washed with water, dried over sodium sulfate and the solvent removed under vacuum.

The crude product is chromatographed on silica gel using n-hexane/diethyl ether 20/80 to yield 0.25 g of pure 6-methylenandrosta-1,4-diene-17β-ol-3-one m.p. 135°–136° C. λ max 247 mµ (ε13.750). Found: C 80.01, H 8.95. $C_{20}H_{24}O_2$ requires: C 80.49, H 8.78.

Following the above described procedure the following compounds can be prepared:
1-methyl-6-methylenandrosta-1,4-diene-17β-ol-3-one;
1-ethyl-6-methylenandrosta-1,4-diene-17β-ol-3-one;
4-methyl-6-methylenandrost-1,4-diene-17β-ol-3-one;
4-ethyl-6-methylenandrosta-1,4-diene-17β-ol-3-one;
6-ethylidenandrosta-1,4-diene-17β-ol-3-one;
6-propylidenandrosta-1,4-diene-17β-ol-3-one and
1-methyl-6-ethylidenandrosta-1,4-diene-17β-ol-3-one

EXAMPLE 2

A solution of 4,5-epoxy-6-methylenandrost-1-ene-17β-ol-3-one (1.0 g) in glacial acetic acid (10 ml) is treated with gaseous hydrogen chloride for 30 min at room temperature.

The precipitate is filtered off, washed with diethyl ether, dried and chromatographed on silica gel using hexane/ethyl acetate to yield 0.8 g of pure 4-chloro-6-methylenandrosta-1,4-diene-17β-ol-3-one. Found: C 72.35, H 7.35, Cl 10.58; $C_{20}H_{25}ClO_2$ requires: C 72.18, H 7.52, Cl 10.68.

MS (m/z): 332.

Following the above reported procedure and starting from the appropriate 4,5-epoxy derivative and using the appropriate gaseous hydrohalic acid, the following compounds can be prepared:
4-bromo-6-methylenandrosta-1,4-diene-17β-ol-3-one;

4-fluoro-6-methylenandrosta-1,4-diene-17β-ol-3-one;
4-chloro-1-methyl-6-methylenandrosta-1,4-diene-17β-ol-3-one;
4-bromo-1-methyl-6-methylenandrosta-1,4-diene-17β-ol-3-one;
4-fluoro-1-methyl-6-methylenandrosta-1,4-diene-17β-ol-3-one;
4-chloro-6-ethylidenandrosta-1,4-diene-17β-ol-3-one;
4-bromo-6-ethylidenandrosta-1,4-diene-17β-ol-3-one;
4-fluoro-6-ethylidenandrosta-1,4-diene-17β-ol-3-one; and
4-chloro-7-methylenandrosta-1,4-diene-17β-ol-3-one.

EXAMPLE 3

A stirred mixture of 5.31 g (0,177 mol) of paraformaldehyde and 17.32 g (0,212 mol) of dimethylamine hydrochloride in 200 ml of isopentanol is refluxed (temperature of about 131° C.) under nitrogen atmosphere in a flask fitted with a Dean-Stark separator. About 60 ml of a mixture of isopentanol and separated water are collected and discarded. The internal reaction temperature is then lowered of 10°-15° C. and 4,55 g (0,016 -ol) of boldenone (i.e. androsta-1,4-dien-17β-ol-3-one) are added to the reaction mixture, which is again heated at reflux for 15 hours.

After cooling, the mixture is treated with 60 ml of a 0.1N NaOH solution and stirred for 30 min. The organic phase is separated, washed with water and evaporated under vacuum (external temperature of 80° C.) to yield about 80 ml of a suspension. The surnatant liquor is separated; the resulting precipitate is washed twice with 10 ml portions of hexane and then crystallized from 25 ml of a mixture of ethanol and water (70:30). The filtered white precipitate is dried under vacuum at 40° C., thus obtaining 1,55 g (0,0052 mol) of 6-methylenandrost-1,4-diene-17β-ol-3-one, m.p. 135°-137° C.

According to the above described procedure and starting from the appropriate compound of formula (II) one can prepared also the following 7- and/or 16-substituted derivatives as single epimers or as a mixture thereof 1,7-dimethyl-16-fluoro-6-methylenandrosta-1,4-dien-17β-ol-3-one;
16-fluoro-6-methylenandrosta-1,4-dien-17β-ol-3-one;
16-fluoro-1-methyl-6-methylenandrosta-1,4-dien-17β-ol-3-one;
1,7-dimethyl-6-methylenandrosta-1,4-dien-17β-ol-3-one;
16-fluoro-7-methyl-6-methylenandrosta-1,4-diene-17β-ol-3-one;
4,16-difluoro-1,7-dimethyl-6-methylenandrosta-1,4-dien-17β-ol-3-one and
7-methyl-6-methylenandrost-1,4-diene-17β-ol-3-one.

EXAMPLE 4

A mixture of sodium acetate (1 g), absolute chloroform (30 ml), formaldehyde-diethylacetal (30 ml, 0.24 mol), phosphoryl chloride (3.8 ml, 0.04 mol), and 1β-methyl-androst-4-ene-17β-ol-3-one-17-acetate (0,93 g 2,7 mmol) is stirred at reflux for about 7 hours, i.e. until disappearance of the starting material. The suspension is allowed to cool and under vigorous stirring a saturated sodium carbonate solution is added dropwise until the pH of the aqueous layer became alkaline (~1 hour). The organic layer is separated, neutralized with water, and dried with sodium sulfate. After concentration under reduced pressure the oily residue is purified by chromatography on silica gel using hexane/ethylacetate as eluent. Thus the pure 1β-methyl-6-methylenandrost-4-ene-17β-ol-3-one-17-acetate is obtained (0,575 g).

I.R. (KBr): 3100 (6=CH$_2$), 1725(17-acetoxy)1680 (3-oxo), 1630, 1660 cm$^{-1}$ (Δ$^4$ and 6=CH$_2$).

By proceeding analogously the following compounds can be prepared:
1β-ethyl-6-methylenandrost-4-ene-17β-ol-3-one-17-acetate;
1β-methyl-6-ethylidenandrost-4-ene-17β-ol-3-one-17-acetate; and
1β-ethyl-6-ethylidenandrost-4-ene-17β-ol-3-ene-17-acetate.

EXAMPLE 5

6-methylenandrost-4-ene-17β-ol-3-one (5 g) is dissolved in 200 ml of methanol and cooled to 0° C. Thereupon ice cold 36% H$_2$O$_2$(17 ml) and 2% NaOH (9 ml) are added.

The mixture is stirred for 1 hour, allowed to stand at 5° C. for 20 hours and then poured into 1400 ml of ice water with vigorous stirring, the product is filtered off, washed with water and dried to give 4.2 (80%) of 4,5-epoxy-6-methylenandrosta-17β-ol-3-one [α/β-epoxyde mixture].

4,5-Epoxy-6-methylenandrosta-17β-ol-3-one (3 g) and dichlorodicyanobenzoquinone (1.7 g) dissolved in 60 ml of anhydrous dioxane are heated to reflux for about 15 hours. The cooled solution is filtered through alumina and the solvent evaporated in vacuo. The residue is taken up with ethylacetate, the organic layer washed with water, dried and the solvent removed under vacuum. The crude product is chromatographed on silica gel using hexane/ethylacetate to yield 1.5 g of pure 4,5-epoxy-6-methylenandrost-1-ene-17β-ol-3-one N.M.R. δ p.p.m.: 0.77 (3H, s); 1.13 (3H, s); 3.71 (1H, d); 3.75 (1H, m); 5.03 (2H, m); 5.86 (1H, d); 6.78 (1H, d).

Following the above described procedure and using the appropriate 6-alkylidenandrost-4-ene-3,17-dione the following compounds can be prepared:
1-methyl-4,5-epoxy-6-methylenandrost-1-ene-17β-ol-3-one;
1-ethyl-4,5-epoxy-6-methylenandrost-1-ene-17β-ol-3-one;
4,5-epoxy-6-ethylidenandrost-1-ene-17β-ol-3-one;
1-methyl-4,5-epoxy-6-ethylidenandrost-1-ene-17β-ol-3-one; and
1-ethyl-4,5-epoxy-6-ethylidenandrost-1-ene-17β-ol-3-one.

EXAMPLE 6

A solution of 6-methylenandrost-1,4-diene-17β-ol-3-one (1.0 g) in pyridine (10 ml) is treated at 5° C. with propionylchloride (1,08 ml). The reaction mixture is allowed to stand with stirring at room temperature overnight. Then it's poured into a water-ice mixture and the product isolated by ethylacetate extraction.

The organic extracts are washed with 2N hydrochloric acid, water, dried (Na$_2$SO$_4$) and evaporated.

The resulting raw product is crystallized from n-hexane/ether to yield 0,95 g of 6-methylenandrost-1,4-diene-17β-ol-3-one-17-propionate m.p. = 123°-125° C.

N.M.R. p.p.m: 0,88 (3H, s); 1,17 (6H, s+t); 2,35 (2H, m); 4,66 (1H, m); 5.02 (2H, m); 6,25 (2H, m); 7.09 (1H, d).

By proceeding analogously and starting from the appropriate steroids, the following compounds can be prepared:
6-methylenandrost-1,4-diene-17β-ol-3-one-17-acetate;

6-methylenandrost-1,4-diene-17β-ol-3-one-17-valerate;
6-methymenandrost-1,4-diene-17β-ol-3-one-17-cyclopentylpropionate;
6-methylenandrost-1,4-diene-17β-ol-3-one-17-oleate;
6-methylenandrost-1,4-diene-17β-ol-3-one-17-hemisuccinate;
1-methyl-6-methylenandrost-1,4-diene-17β-ol-3-one-17-acetate;
1-methyl-6-methylenandrost-1,4-diene-17β-ol-3-one-17-propionate;
1-methyl-6-methylenandrost-1,4-diene-17β-ol-3-one-17-valerate;
1-methyl-6-methylenandrost-1,4-diene-17β-ol-3-one-17-undecylate;
1-methyl-6-methylenandrost-1,4-diene-17β-ol-3-one-17-cyclopentylpropionate;
1-methyl-6-methylenandrost-1,4-diene-17β-ol-3-one-17-oleate;
1-methyl-6-methylenandrost-1,4-diene-17β-ol-3-one-17-hemisuccinate;
6-methylenandrost-1,4-diene-17β-ol-3-one-17-undecylate; and
7-methyl-6-methylenandrost-1,4-diene-17β-ol-3-one-17-propionate.

EXAMPLE 7

Phosphoryl chloride (0.13 ml) is added to a solution of 6-methylenandrosta-1,4-diene-17β-ol-3-one (2,5 g) in 2,3-dihydropyran (10 ml). After being allowed to stand for 4 hrs. at 18° C., the solution is diluted with ether, washed with aqueous sodium carbonate and water, dried over sodium sulphate and evaporated to dryness under vacuum. The oily residue is purified by chromatography on silica gel using hexane/ethyl acetate as eluent.

Thus the pure 17β-(tetrahydropyran-2'-yloxy)-6-methylenandrosta-1,4-dien-3-one is obtained (2,66 g)

Found: C 78.49, H 8.84. $C_{25}H_{34}O_3$ requires: C 78.53, H 8.90.

According to the above described procedure and starting from the appropriate compound, the following compounds can be prepared:
17β-(tetrahydropyran-2'-yloxy)-6-ethyldenandrosta-1,4-diene-3-one;
17β-(tetrahydropyran-2'-yloxy)-1-methyl-6-methylenandrosta-1,4-diene-3-one;
17β-(tetrahydropyran-2'-yloxy)-1-methyl-6-ethylidenandrosta-1,4-diene-3-one;
17β-(tereahydropyran-2'-yloxy)-7-methyl-6-methylenandrosta-1,4-diene-3-one;
17β-(tetrahydropyran-2'-yloxy)-7-methyl-6-ethylidenandrosta-1,4-diene-3-one;
17β-(tetrahydropyran-2'-yloxy)-1,7-dimethyl-6-methylenandrosta-1,4-diene-3-one and
17β-(tetrahydropyran-2'-yloxy)-1,7-dimethyl-6-ethylidenandrosta-1,4-dien-3-one;

EXAMPLE 8

To a solution of 6-methylenandrosta-1,4-diene-17β-ol-3-one (1,2 g, 4 mmol) in pyridine (40 ml) a catalytic amount of 4-dimethylamino-pyridine is added.

The stirred mixture, cooled at −15° C., is treated with chlorosulphonic acid (1,33 ml, 20 mmol), allowed to stand for 4 hours at room temperature and then diluted with sodium hydroxide solution.

The aqueous solution is washed with ethyl ether, acidified with 2N hydrochloric acid and extracted with methylene chloride. The organic extracts are dried over $Na_2SO_4$ and evaporated at reduced pressure so obtaining 0,95 g of quite pure 6 methylenandrosta-1,4-diene-17β-ol-3-one-17-sulphate N.M.R. δ p.p.m.: 0.75 (3H, s); 1.05 (3H, s), 4.05 (1H, m); 4,85 (2H, m); 5,9 (1H, d); 5,97 (1H, dd); 6,82 (1H, d).

According to the above described procedure the following compounds can be prepared:
6-ethylenandrosta-1,4-diene-17β-ol-3-one-17-sulphate;
1-methyl-6-methylenandrosta-1,4-diene-17β-ol-3-one-17-sulphate;
1-methyl-6-ethylidenandrosta-1,4-diene-17β-ol-3-one-17-sulphate;
7-methyl-6-methylenandrosta-1,4-diene-17β-ol-3-one-17-sulphate and
7-methyl-6-ethylidenandrosta-1,4-dien-17β-ol-3-one-17-sulphate.

EXAMPLE 9

6-methylenandrosta-1,4-diene-17β-ol-3-one-17-sulphate (1.80 g; 0.005 mol) is dissolved in 0.5N ethanolic NaOH (10 ml). The solution is diluted with acetone. After ten minutes the resulting sodium salt is collected by filtration and washed with ethyl ether.

Found: C 59,87% H 6,31% Na 5.71% S 7.94%. $C_{20}H_{25}NaO_5S$ requires: C 60.00%, H 6.25%, Na 5,75%, S 8.00%.

Analogously the sodium salt of the following compounds can be prepared;
6-ethylidenandrosta-1,4-diene-17β-ol-3-one-17-sulphate;
1-methyl-6-methylenandrosta-1,4diene-17β-ol-3-one-17-sulphate and
1-methyl-6-ethylidenandrosta-1,4-diene-17β-ol-3-one-17-sulphate.

EXAMPLE 10

Tablets each weighing 0.150 g and containing 25 mg of the active substance, can be manufactured as follows:

| Composition (for 10000 tablets) | |
|---|---|
| 6-methylenandrosta-1,4-diene-17 β-ol-3-one | 250 g |
| Lactose | 800 g |
| Corn starch | 415 g |
| Talc powder | 30 g |
| Magnesium stearate | 5 g |

The 6-methylenandrosta-1,4-diene-17β-ol-3-one- the lactose and half the corn starch are mixed; the mixture is then forced throught a sieve of 0.5 mm mesh size. Corn starch (10 g) is suspended in warm water (90 ml) and the resulting paste is used to granulate the powder.

The granulate is dried, comminuted on a sieve of 1.4 mm mesh size, then the remaining quantity of starch, talc and magnesium stearate is added, carefully mixed and processed into tablets.

EXAMPLE 11

Capsules, each dosed at 0.200 g and containing 20 mg of the active substance can be prepared.

| Compositin for 500 capsules | |
|---|---|
| 6-methylenandrosta-1,4-diene-17 β-ol-3-one | 10 g |
| Lactose | 80 g |
| Corn starch | 5 g |
| Magnesium stearate | 5 g |

We claim:

1. A compound of general formula (I)

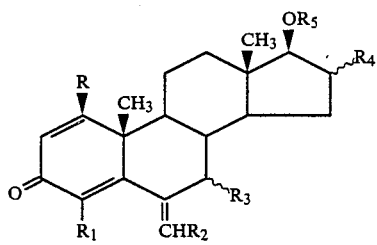

wherein
each of R and $R_3$, independently, is hydrogen or $C_1$–$C_6$ alkyl;
$R_1$ is hydrogen, halogen or $C_1$–$C_6$ alkyl;
$R_2$ is hydrogen or $C_1$–$C_6$ alkyl;
$R_4$ is hydrogen or fluorine;
$R_5$ is (a) hydrogen or $C_1$–$C_6$ alkyl; (b) phenyl unsubstituted or substituted by one or two substituents independently chosen from $C_1$–$C_6$ alkyl, halogen and amino; (c) an acyl group; or (d) a hydroxy protecting group; and the pharmaceutically acceptable salts thereof.

2. A compound of formula (I) according to claim 1, wherein
R and $R_3$ are independently hydrogen or $C_1$–$C_4$ alkyl;
$R_1$ is hydrogen, fluorine, chlorine or $C_1$–$C_4$ alkyl;
$R_2$ is hydrogen or $C_1$–$C_4$ alkyl;
$R_4$ is hydrogen or fluorine;
$R_5$ is hydrogen, $C_1$–$C_4$ alkyl or an acyl group deriving from an acid selected from the group comprising acetic, propionic, valeric, undecylic, phenylacetic, cyclopentylpropionic, oleic, aminoacetic, succinic, sulphuric and phosphoric acid; and the pharmaceutically acceptable salts thereof.

3. A pharmaceutical composition containing a suitable carrier and/or diluent and, as an active principle, a compound of formula (I) according to claim 1 or a pharmaceutically acceptable salt thereof.

4. A pharmaceutical composition, suitable for the treatment of hormone-dependent diseases in patients in need thereof comprising, as an active principle, a therapeutically effective amount of a compound of formula (I), according to claim 1, in association with a suitable carrier and/or diluent.

5. A pharmaceutical composition, suitable for the treatment of hormone-dependent breast, pancreatic, endometrial and ovarian cancers comprising, as an active principle, a therapeutically effective amount of a compound of formula (I), according to claim 1, in association with a suitable carrier and/or diluent.

6. A method for the treatment of hormone-dependent diseases in patients in need thereof, said method comprising administering to said patients an effective amount of a compound of claim 1.

7. A method for the treatment of hormone-dependent breast, pancreatic, endometrial and ovarian cancers, said method comprising administering to said patients an effective amount of a compound of claim 1.

8. A compound selected from the group consisting of:
6-methylenandrosta-1,4-diene-17β-ol-3-one;
1-methyl-6-methylenandrosta-1,4-diene-17β-ol-3-one;
7-methyl-6-methylenandrosta-1,4-diene-17β-ol-3-one;
4-chloro-6-methylenandrosta-1,4-diene-17β-ol-3-one;
4-chloro-1-methyl-6-methylenandrosta-1,4-diene-17β-ol 3-one:
4-chloro-7-methyl-6-methylenandrosta-1,4-diene-17β-ol-3-one;
6-methylenandrosta-1,4-diene-17β-ol-3-one-17-propionate;
1-methyl-6-methylenandrosta-1,4-diene-17β-ol-3-one-17-propianate;
7-methyl-6-methylenandrosta-1,4-diene,17β-ol-3-one-17-propionate;
6-methylenandrosta-1,4-diene-17β-ol-3-one-17-sulphate;
1-methyl-6-methylenandrosta-1,4-diene-17β-ol-3-one-17-sulphate; and
7-methyl-6-methylenandrosta-1,4-diene-17β-ol-3-one-17-sulphate; and
where appropriate, the pharmaceutically acceptable salts thereof.

* * * * *